(12) United States Patent
Lowman

(10) Patent No.: US 9,861,461 B2
(45) Date of Patent: Jan. 9, 2018

(54) STABILIZER FOR THE TRANSVAGINAL PLACEMENT OF A MIDURETHRAL SLING

(71) Applicant: Joye Lowman, Atlanta, GA (US)

(72) Inventor: Joye Lowman, Atlanta, GA (US)

( * ) Notice: Subject to any disclaimer, the term of this patent is extended or adjusted under 35 U.S.C. 154(b) by 209 days.

(21) Appl. No.: 14/254,385

(22) Filed: Apr. 16, 2014

(65) Prior Publication Data

US 2015/0133726 A1     May 14, 2015

Related U.S. Application Data

(60) Provisional application No. 61/902,572, filed on Nov. 11, 2013.

(51) Int. Cl.
*A61F 2/00*         (2006.01)

(52) U.S. Cl.
CPC .................................. *A61F 2/0045* (2013.01)

(58) Field of Classification Search
CPC .............................. A61F 2/0045; A61C 5/90
USPC ........................................................... 600/30
See application file for complete search history.

(56) References Cited

U.S. PATENT DOCUMENTS

| | | | | |
|---|---|---|---|---|
| 1,498,267 A * | 6/1924 | Hachman | ............... | A61C 17/02 433/89 |
| 5,730,597 A * | 3/1998 | Luttrell | .................... | A61O 5/90 433/140 |
| 6,702,827 B1 * | 3/2004 | Lund | .................. | A61B 17/1227 600/29 |
| 6,939,134 B2 * | 9/2005 | Sherry | ..................... | A61O 5/90 433/140 |
| 8,784,101 B1 * | 7/2014 | Engeron | .................. | A61C 5/90 433/140 |
| 2003/0212305 A1 * | 11/2003 | Anderson | .......... | A61B 17/0401 600/29 |
| 2004/0111102 A1 * | 6/2004 | Saller | ..................... | A61B 17/00 606/151 |
| 2004/0116944 A1 * | 6/2004 | Chu | ...................... | A61F 2/0045 606/151 |

* cited by examiner

*Primary Examiner* — Christine H Matthews
*Assistant Examiner* — Kaylee Wilson
(74) *Attorney, Agent, or Firm* — Fisherbroyles, LLP

(57) ABSTRACT

A sling for stress urinary incontinence (SUI) may be placed and stabilized using a midurethral sling stabilizer. First, a sling may be placed beneath the urethra in a position to support the urethra, without tension. The midurethral sling stabilizer may then be inserted in a manner where the distal end partially encompasses and stabilizes the sling through a partial aperture and stabilizes the sling in a desired position, without tension. Once the sling is stabilized in the desired position, the sheath may be removed from the sling.

4 Claims, 5 Drawing Sheets

US 9,861,461 B2

STABILIZER FOR THE TRANSVAGINAL PLACEMENT OF A MIDURETHRAL SLING

CROSS-REFERENCE TO RELATED APPLICATIONS

This patent application claims priority to U.S. Patent Application Ser. No. 61/902,572, filed Nov. 11, 2013 and entitled "Stabilizer for the Transvaginal Placement of a Midurethral Sling," of which the disclosure is incorporated herein, in its entirety, by reference.

TECHNICAL FIELD

The present disclosure relates generally to a method and device for optimal placement of a midurethral sling.

BACKGROUND

Stress urinary incontinence (SUI) primarily affects women, but may be common in men as well. SUI may be caused by intrinsic sphincter deficiency (ISD) or hypermobility. These conditions may occur independently or in combination. In ISD, the urinary sphincter fails to close properly, causing urine to leak out of the urethra during stressful activity. Hypermobility is a condition in which the bladder neck and proximal urethra rotate and descend in response to increases in intra-abdominal pressure (e.g., due to sneezing, coughing, laughing, etc.). As a result, the patient's response time becomes insufficient to promote urethral closure and, consequently, the patient suffers from urine leakage.

Midurethral slings are a common treatment for SUI. Midurethral slings work optimally when placed without tension, just underneath the midurethra. A plastic sheath protects the sling and allows it to be adjusted during placement. Once the midurethral sling (i.e., sling) is placed in an optimal position, the plastic sheath is removed. However, removal of the plastic sheath may cause the sling to move cephalad (i.e., towards the head or anterior end of the body) or to be pulled so that it is no longer free of tension. Removal of the sheath may also cause the sling to roll or fold which may lead to failure or irritative voiding symptoms and/or voiding dysfunction. It is with respect to these considerations and others that the various embodiments of the present invention have been made.

BRIEF DESCRIPTION OF THE DRAWINGS

The accompanying drawings, which are incorporated in and constitute a part of this disclosure, illustrate various embodiments of the present disclosure. In the drawings.

SUMMARY

This summary is provided to introduce a selection of concepts in a simplified form that are further described below in the Detailed Description. This summary is not intended to identify key features or essential features of the claimed subject matter, nor is it intended as an aid in determining the scope of the claimed subject matter.

The use of a midurethral sling stabilizer for stabilizing a sling before and after removing a sheath (which may be made of plastic), is disclosed. Initially, a sling is placed beneath the urethra in a position to support the urethra. The midurethral sling stabilizer may be inserted in a manner where the distal end partially encompasses the sling through a partial aperture and stabilizes the sling in a desired position, without tension. Once the sling is stabilized in the desired position, the sheath may be removed from the sling. Finally, the sling may be left in the body of the patient to support the urethra.

These and other features and advantages will be apparent from a reading of the following detailed description and a review of the associated drawings. It is to be understood that both the foregoing general description and the following detailed description are illustrative only and are not restrictive of the invention as claimed.

DETAILED DESCRIPTION

In the following detailed description, references are made to the accompanying drawings that form a part hereof, and in which are shown by way of illustrations specific embodiments or examples. These embodiments may be combined, other embodiments may be utilized, and structural changes may be made without departing from the spirit or scope of the present invention. The following detailed description is therefore not to be taken in a limiting sense.

Figure 1:
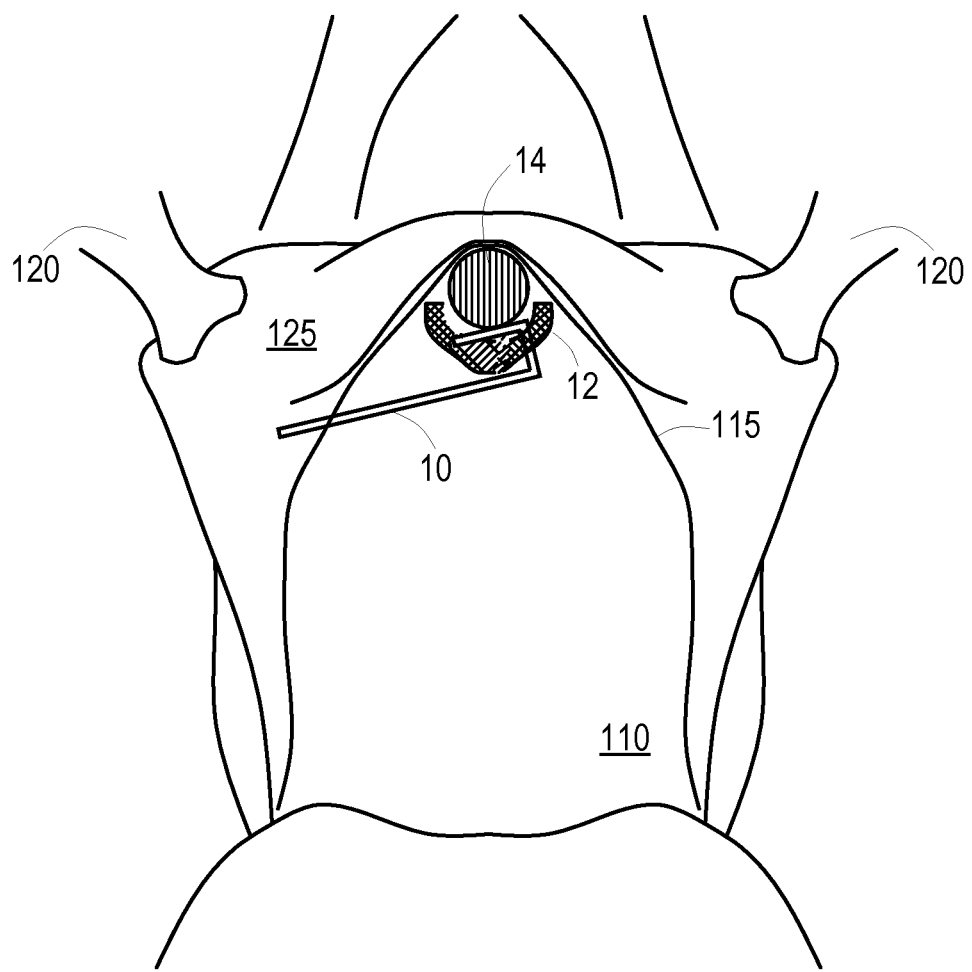
FIG. 1 schematically depicts a sling implanted at an anatomical site of a patient and which is stabilized using a midurethral sling stabilizer, in accordance with an embodiment.

Referring now to the drawings, in which like numerals represent like elements through the several figures, various aspects of the present invention will be described. FIG. 1 schematically depicts a midurethral sling 12 (referred to herein as "the sling 12") implanted at an anatomical site in a patient and stabilized using a midurethral sling stabilizer 10, in accordance with an embodiment. As shown in FIG. 1, the sling 12 may be placed at a midurethral location in periurethral tissue in the patient and an incision 115 may be made in vaginal wall 125. The incision 115 permits a surgeon performing a procedure to access urethra 14, by creating an opening 110 beneath the urethra 14 to separate vaginal tissue. To perform the procedure, the surgeon may clip the separated vaginal tissues so that they are held apart using clips 120. This allows the surgeon to be able to access the urethra 14 through the opening 110 created by the incision 115. The surgeon may then introduce the sling 12 into the body using medical instruments, such as trocars, so that it lies under or in close proximity to the urethra 14. The sling 12 may then be adjusted (as needed) using Credé maneuver or by having the patient cough. At this point, the midurethral sling stabilizer 10 may be utilized (instead of a hemostat, scissors, forceps, medical graspers, etc.) to not only serve as a "spacer" to prevent the sling from being pulled too tight but also to prevent the sling from sliding or rolling and further to prevent the sling from being too loose, when a sheath (not shown) which covers the sling 12, is removed. It should be understood that the sling 12 is pulled too tight when there is tension induced or applied to the sling 12. It should further be understood that the sling 12 is too loose when it is no longer under or in close proximity to the urethra 14. It should be appreciated that other medical instruments, such as hemostats, scissors, forceps, medical graspers, etc. are non-optimal as sling stabilizers because their size or other structural limitations are more likely to cause the sling to be pulled too tight, become too loose, roll or slide, during the procedure described above.

Figure 2A:
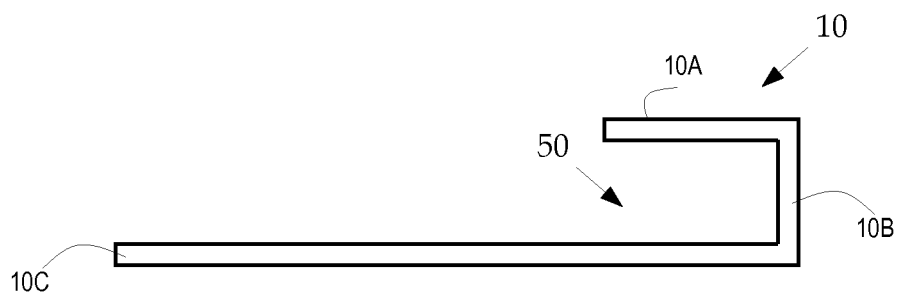
FIGS. 2A-2E depict side and perspective views of the midurethral sling stabilizer of FIG. 1, in accordance with various embodiments.
Figure 2B:
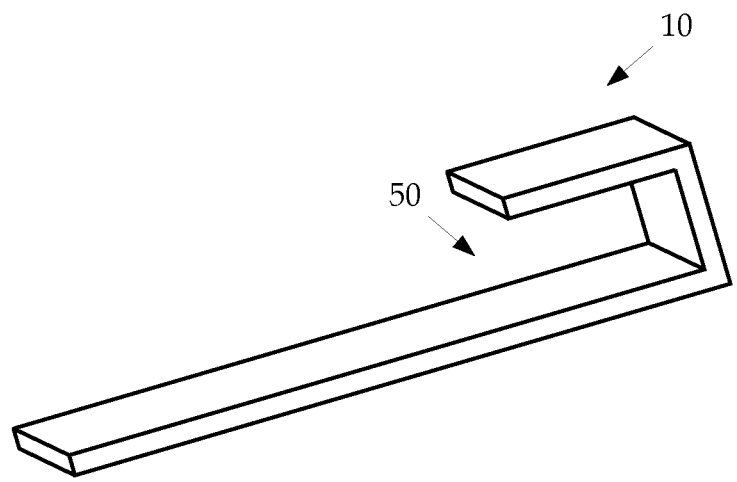
Figure 2C:
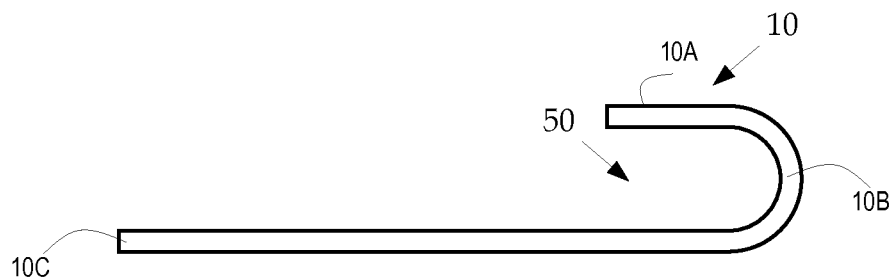
Figure 2D:
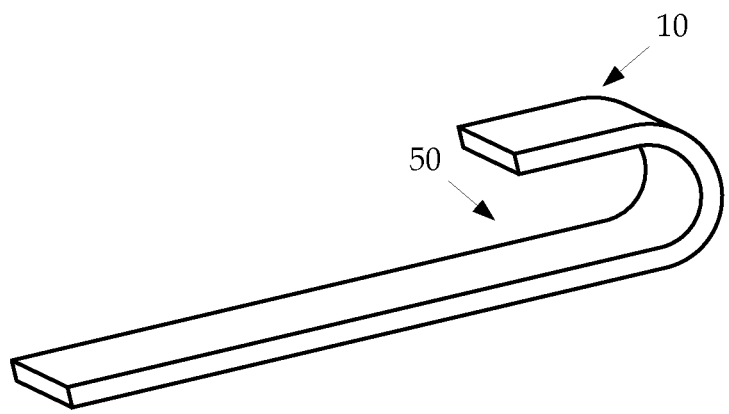
Figure 2E:
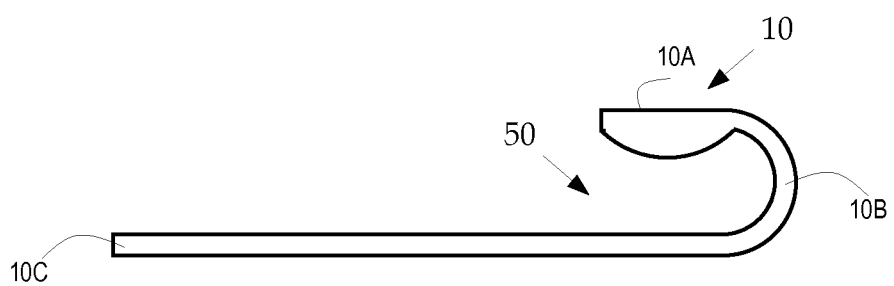

FIGS. 2A-2E depicts the midurethral sling stabilizer 10 for stabilizing the sling 12, in accordance with various embodiments. The midurethral sling stabilizer 10 may be an elongated device having a distal end which comprises a partial aperture 50. In accordance with various embodiments, the partial aperture 50 may be square-shaped as shown in FIGS. 2A and 2B or rounded as shown in FIGS. 2C-2E. It should be understood that the partial aperture 50 may also take any other shape that restricts the sling 12 to moving in one direction of freedom, including, but not limited to, hexagonal, heptagonal and octagonal shapes. The distal end of the midurethral sling stabilizer 10 may encompass the sling 12 through the partial aperture 50 to implant the sling 12 in a desired position, and to stabilize the sling 12 while removing a sheath (e.g., a plastic sheath) from the sling 12. In accordance with various embodiments, the midurethral sling stabilizer 10 may be constructed from stainless steel, silicone, plastic, or other types of medical device material known in the art. In identifying materials for the midurethral sling stabilizer, the material's biocompatibility, qualification, regulation and cost may be considered. Therefore, it should be appreciated that the material for the midurethral sling stabilizer 10 may be the same material as found in other products utilized in surgical procedures for treating stress urinary incontinence (SUI). Turning now to FIG. 2A, in one embodiment, a short or top end 10A of the midurethral sling stabilizer 10 may be approximately 1 to 3 centimeters long, a connecting end 10B of the midurethral sling stabilizer 10 may be approximately 0.1 to 1.5 centimeters high, and a long or bottom end 10C may be approximately 5 to 20 centimeters long. The midurethral sling stabilizer 10 may also have a uniform thickness which may be approximately 0.1 to 1.5 centimeters. It should be understood that the aforementioned dimensions may also be similar for the alternative embodiments of the midurethral sling stabilizer 10 shown in FIGS. 2C and 2E with respect to the top end 10A, the connecting end 10B and the bottom end 10C. It should further be understood that the top end 10A of the midurethral sling stabilizer 10 shown in FIG. 2E may further have a beveled bottom edge.

It should be understood that the top end 10A of the midurethral sling stabilizer 10 (as described above with respect to the FIGS. 2A, 2C and 2E) may lie beneath the urethra 14 and act as a "spacer" to prevent the sling 12 from being pulled too tight (i.e., preventing tension from being induced to the sling 12) during use. For example, the beveled top end 10A shown in FIG. 2E may be utilized to create room between the sling 12 and the urethra 14 to assist in the sling 12 from being pulled to tightly during use. It should further be understood that the connecting end 10B of the mideurethral sling stabilizer 10 may be placed behind the sling 12 to prevent the sling 12 from sliding cephalad (i.e., towards the head or anterior end of the body).

Figure 3:
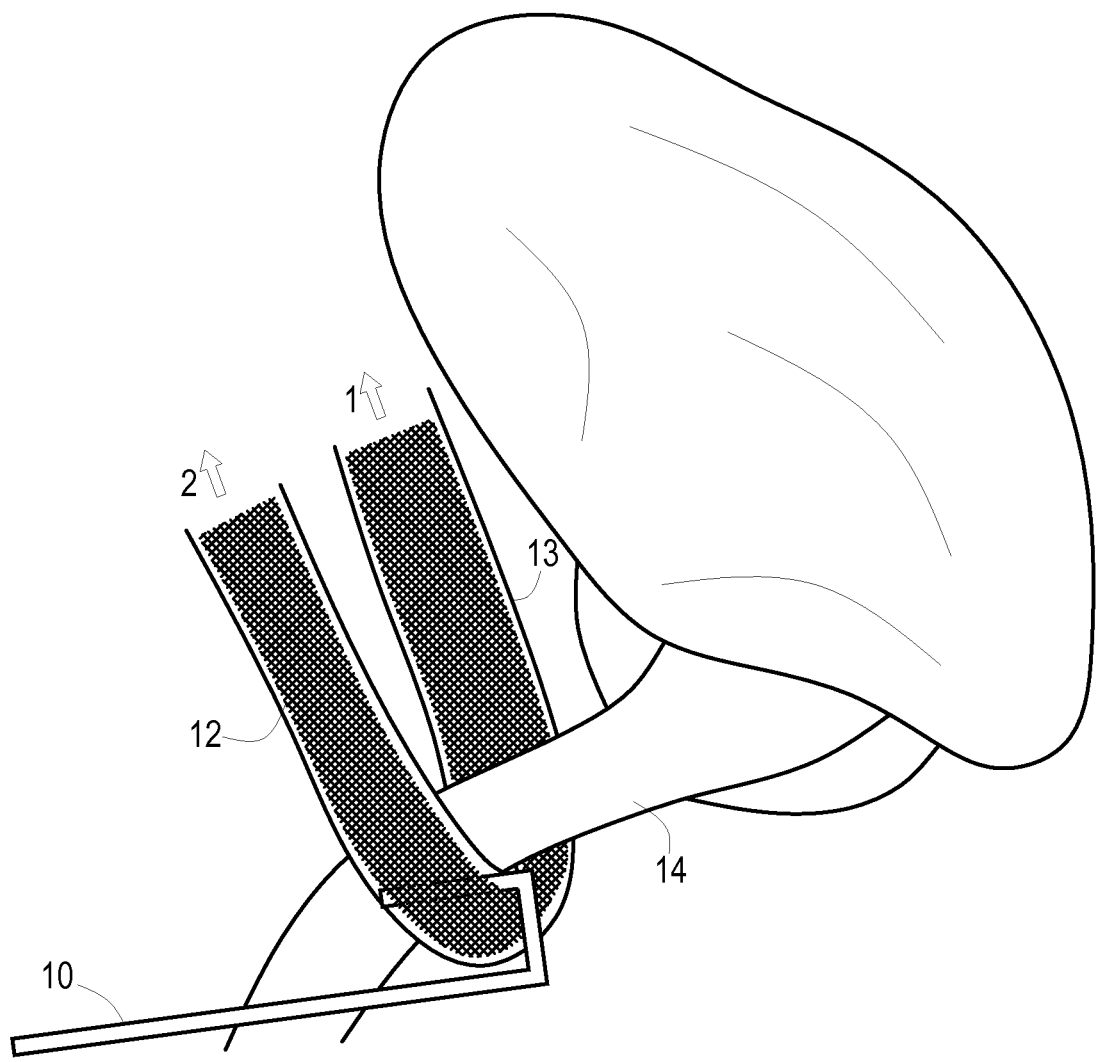
FIG. 3 schematically depicts a sling which is covered by a sheath, which is implanted at an anatomical site of a patient and which is stabilized using a midurethral sling stabilizer, in accordance with an embodiment.

FIG. 3 schematically depicts the sling which is covered by a sheath 13, which is implanted at an anatomical site of a patient and which is stabilized using the midurethral sling stabilizer 10, in accordance with an embodiment. After the surgeon has passed the sling 12 through an opening in a vaginal wall of the patient, the sling 12 may be optimally placed or positioned beneath the urethra 14 in a position to support the urethra 14, without tension. Once the sling 12 is optimally positioned in a manner where it is free of tension beneath the urethra 14, the midurethral sling stabilizer 10 may be introduced to maintain the sling 12's position. It should be understood that optimal placement of the sling 12 may be achieved when the sling 12 lies under the urethra 14 without tension but in close enough proximity to the urethra 14 that the sling 12 closes the urethra 14 during increases in intra-abdominal pressure. Appropriate placement may also be determined in response to asking the patient to cough or in response to performing Credé's maneuver for testing the position of the sling 12. Once it has been determined that the patient no longer leaks (e.g., urine) or leaks nominally, optimal placement has been achieved. After stabilizing the sling 12, the sheath 13 may be removed by pulling the sheath 13 off the sling 12. To avoid inducing tension to the sling 12, the midurethral sling stabilizer 10 may be inserted to partially encompass the sling 12 while stabilizing the sling 12 below the urethra 14. Removal of the sheath 13 may be achieved by sliding the sheath 13 from the sling 12 in the direction indicated by the arrows 1 and 2. The sling 12 is still stabilized within the partial aperture 50 of the midurethral sling stabilizer 10, without tension, while removing the sheath 13 from the sling 12.

Figure 4:
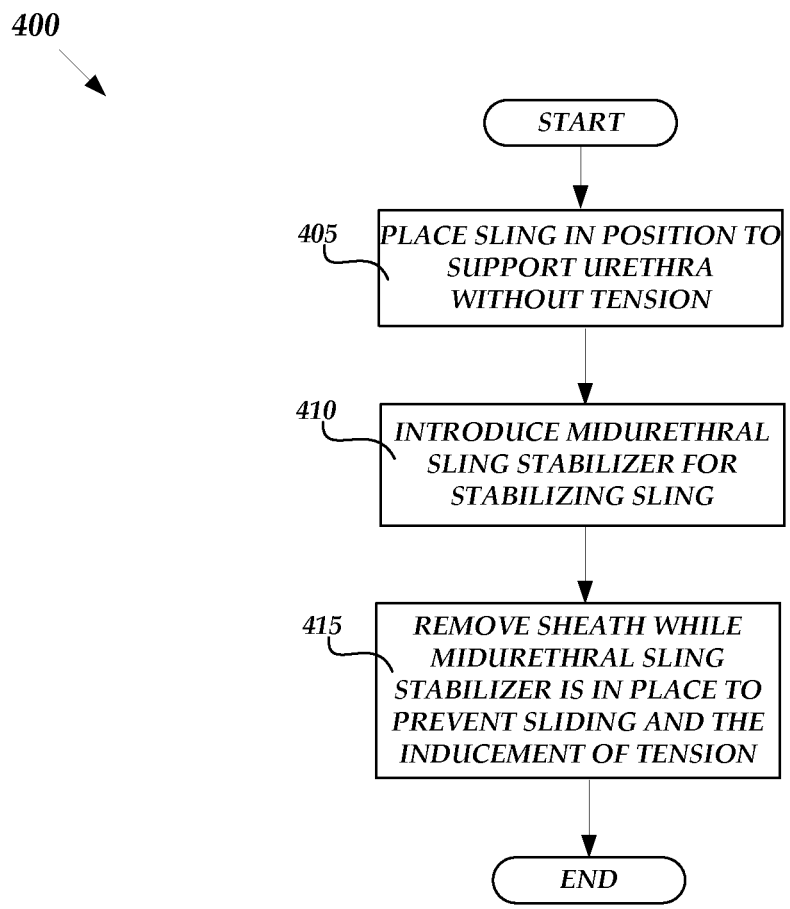
FIG. 4 is a flowchart setting forth the general stages involved in a method consistent with an embodiment of the disclosure for implanting and stabilizing a sling.

FIG. 4 is a flow chart setting forth the general stages involved in a method 400 consistent with an embodiment of the disclosure for implanting and stabilizing the sling. The method 400 may be implemented using the midurethral sling stabilizer 10 as described in more detail above with respect to FIGS. 1-3. Techniques for implementing the stages of the method 400 will be described in greater detail below.

The method 400 may begin at starting block 405 and proceed to stage 415. At stage 405, the sling 12 may optimally be placed beneath the urethra 14 in a position to support the urethra 14, without tension. For example, a surgeon may place the sling 12 beneath the urethra 14 using a hemostat, scissors, forceps, or medical graspers. Alternatively, the surgeon may place the sling 12 beneath the urethra 14 using the midurethral sling stabilizer 10 disclosed herein.

From stage 405, the method 405 may continue to stage 410 where the midurethral sling stabilizer 10 may be inserted in a manner where the distal end partially encompasses the sling 12 through the partial aperture 50 and stabilizes the sling 12 in a desired position, without tension.

From stage 410, where the midurethral sling stabilizer 10 is inserted to stabilize the sling 12, the method 400 may continue to stage 415 where the sheath 13, covering the sling 12, is removed while the midurethral sling stabilizer 12 is in place (i.e., stabilizing the sling 12) to prevent sliding and the inducement of tension on the sling 12. In one embodiment, the sheath 13 may be removed through the partial aperture 50 while the sling 12 is being stabilized by the midurethral sling stabilizer 10. The sheath 13 may be removed by pulling the sheath 13 off the sling 12 in a single direction as indicated in FIG. 3. It should be understood that utilizing the midurethral sling stabilizer 10 allows the sheath 13 to be removed without inducing tension to the sling 12. Thus, the sling 12's position is stabilized within the partial aperture 50 of the midurethral sling stabilizer 10. From stage 415, the method 400 then ends.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed invention.

What is claimed is:

1. A method for utilizing a midurethral sling stabilizer to implant and stabilize a midurethral sling during treatment of urinary incontinence in a patient, comprising:

utilizing at least a partial aperture formed by the midurethral sling stabilizer adapted to place the midurethral sling beneath a urethra of a patient, the partial aperture being formed by a top end, a bottom end, and a non-hinged curved connecting end of the midurethral sling stabilizer, the top end comprising a top edge and a beveled bottom edge, the beveled bottom edge comprising at least a convex portion protruding a distance from the top edge, wherein the bottom end is below the top end, wherein the non-hinged curved connecting end is substantially perpendicular to the top end and the bottom end, the midurethral sling being covered by a sheath;

stabilizing the midurethral sling in the partial aperture, the partial aperture being adapted to support the midurethral sling beneath the urethra of the patient without tension;

removing the sheath from the midurethral sling in a single direction while the midurethral sling is stabilized, wherein the at least the convex portion of the beveled bottom edge of the top end of the midurethral sling stabilizer is adapted to create a space between the midurethral sling and the urethra by depressing the midurethral sling away from the urethra, the space preventing tension from being induced in the midurethral sling during the removal of the sheath.

2. The method of claim 1, wherein the midurethral sling is stabilized such that the midurethral sling is adapted to close the urethra during increases in intra-abdominal pressure in the patient.

3. The method of claim 1, wherein the midurethral sling is stabilized such that the patient no longer leaks urine from the urethra.

4. The method of claim 1, wherein the midurethral sling is stabilized such that the patient leaks a nominal amount of urine from the urethra.

* * * * *